(12) United States Patent
Garcia Saban et al.

(10) Patent No.: US 9,918,808 B2
(45) Date of Patent: Mar. 20, 2018

(54) DENTAL POST FOR SUPPORTING DENTAL PROSTHESES AND METHOD FOR THE PRODUCTION THEREOF

(71) Applicant: PHIBO DENTAL SOLUTIONS, S.L., Sentmenat (barcelona) (ES)

(72) Inventors: Francisco Javier Garcia Saban, Barcelona (ES); Francesc Alsina Font, Barcelona (ES); Daniel Aguilar Garcia, Barcelona (ES)

(73) Assignee: PHIBO DENTAL SOLUTIONS, S.L., Sentmenat (Barcelona) (ES)

( * ) Notice: Subject to any disclaimer, the term of this patent is extended or adjusted under 35 U.S.C. 154(b) by 288 days.

(21) Appl. No.: 14/379,579

(22) PCT Filed: Feb. 19, 2013

(86) PCT No.: PCT/ES2013/070101
§ 371 (c)(1),
(2) Date: Aug. 19, 2014

(87) PCT Pub. No.: WO2013/124510
PCT Pub. Date: Aug. 29, 2013

(65) Prior Publication Data
US 2015/0010883 A1    Jan. 8, 2015

(30) Foreign Application Priority Data

Feb. 20, 2012 (ES) .................................. 201230254

(51) Int. Cl.
*A61C 8/00* (2006.01)
*A61C 9/00* (2006.01)
*A61C 13/00* (2006.01)

(52) U.S. Cl.
CPC ............ *A61C 8/0068* (2013.01); *A61C 8/005* (2013.01); *A61C 8/0056* (2013.01);
(Continued)

(58) Field of Classification Search
CPC ......... A61C 5/10; A61C 8/0051; A61C 8/005; A61C 13/0004; A61C 9/004;
(Continued)

(56) References Cited

U.S. PATENT DOCUMENTS 5,135,395 A    8/1992 Marlin
5,145,372 A    9/1992 Daftary et al.
(Continued)

FOREIGN PATENT DOCUMENTS

EP        0473262 A1      3/1992
MX      2010001829 A      3/2010
WO   WO-2009/025442 A1   2/2009

OTHER PUBLICATIONS

Extended European Search Report issued in European Pat. Appl. No. 13 75 1222 dated Oct. 14, 2015.
(Continued)

*Primary Examiner* — Nicholas Lucchesi
(74) *Attorney, Agent, or Firm* — Marshall, Gerstein & Borun LLP

(57) ABSTRACT

The present invention relates to a dental post for supporting dental prostheses by a screw attachment and method for the manufacture thereof which provides a customizable optimum solution for each case, both from the mechanical viewpoint and from the aesthetic viewpoint, essentially comprising an upper hole into which the retaining screw is screwed for retaining the prosthesis on the post such that the upper hole can be located at any point of the surface of the post once said post has been customized in terms of the shape thereof and type of retention to the prosthesis depending on the mechanical and aesthetic needs of the type of rehabilitation suitable for each particular case.

5 Claims, 9 Drawing Sheets

(52) U.S. Cl.
CPC ........ *A61C 9/0006* (2013.01); *A61C 13/0004* (2013.01); *A61C 13/0015* (2013.01); *A61C 13/0018* (2013.01)

(58) Field of Classification Search
CPC ... A61C 9/0046; A61C 8/0068; A61C 8/0056; A61C 9/0006; A61C 13/0015; A61C 13/0018
USPC ....... 433/172, 173, 174, 176, 214, 220, 221, 433/223
See application file for complete search history.

(56) References Cited

U.S. PATENT DOCUMENTS

| | | | |
|---|---|---|---|
| 5,316,477 A | | 5/1994 | Calderon |
| 5,527,182 A | | 6/1996 | Willoughby |
| 8,425,231 B1 | * | 4/2013 | Hochman ............... A61C 8/008 433/173 |
| 8,545,223 B1 | * | 10/2013 | Cherkinsky .......... A61C 8/0033 433/174 |
| 2007/0092854 A1 | * | 4/2007 | Powell ............... A61C 13/0004 433/213 |
| 2009/0047629 A1 | | 2/2009 | Kim |
| 2009/0104585 A1 | * | 4/2009 | Diangelo ............. A61C 8/0001 433/223 |
| 2009/0319068 A1 | * | 12/2009 | Sager ...................... A61C 5/10 700/98 |
| 2009/0325125 A1 | * | 12/2009 | DiAngelo ............ A61C 8/0001 433/173 |
| 2011/0123954 A1 | | 5/2011 | Yau et al. |
| 2012/0088208 A1 | * | 4/2012 | Schulter ............... A61C 8/0001 433/173 |
| 2015/0073577 A1 | * | 3/2015 | Fisker ...................... A61C 9/00 700/98 |
| 2015/0320520 A1 | * | 11/2015 | Schulter ............... A61C 8/0027 433/29 |
| 2016/0015488 A1 | * | 1/2016 | Miltau ................. A61C 8/0001 433/75 |

OTHER PUBLICATIONS

International Search Report issued in PCT/ES2013/070101 dated Jun. 17, 2013.

* cited by examiner

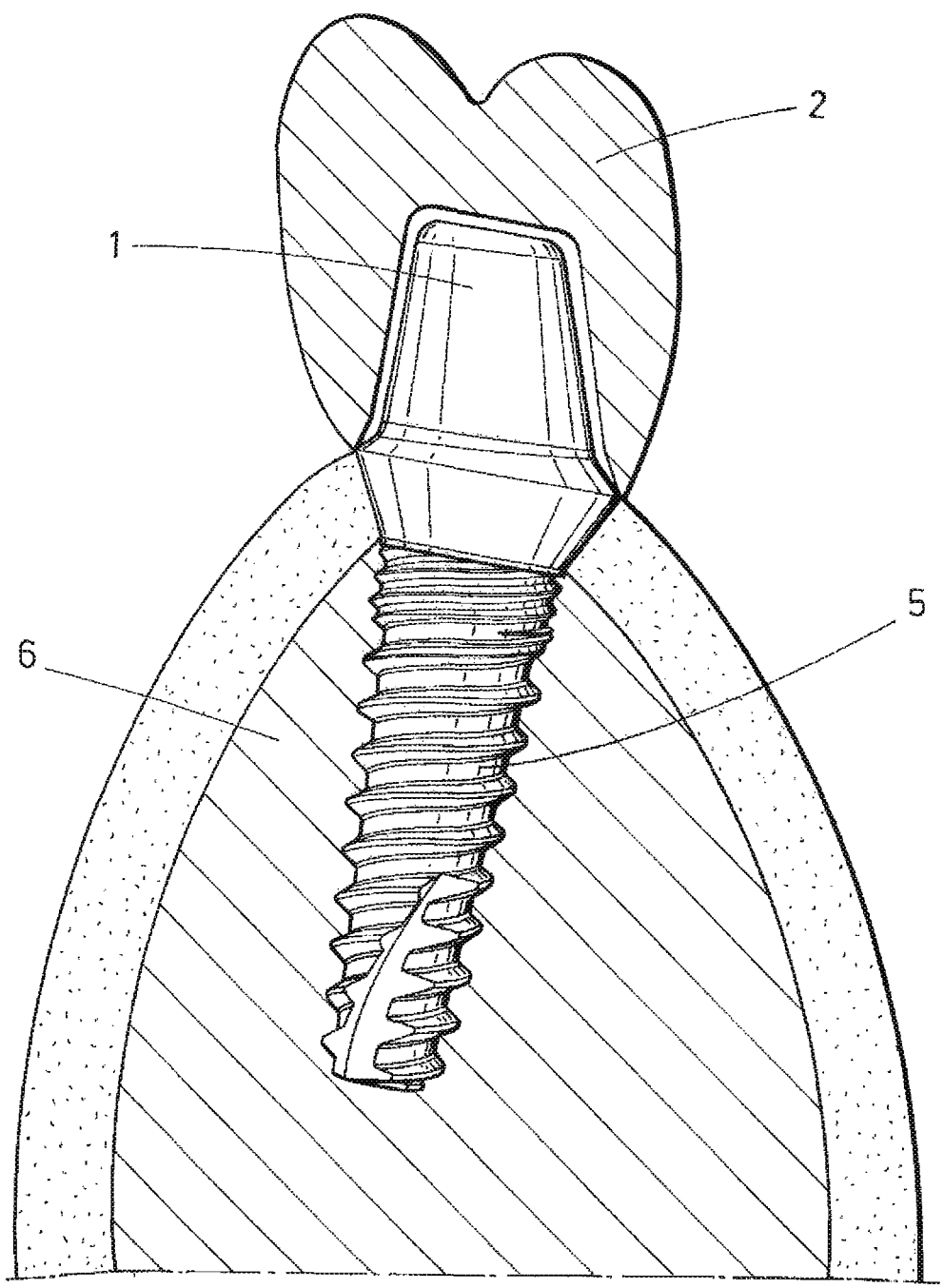
FIG.3.1

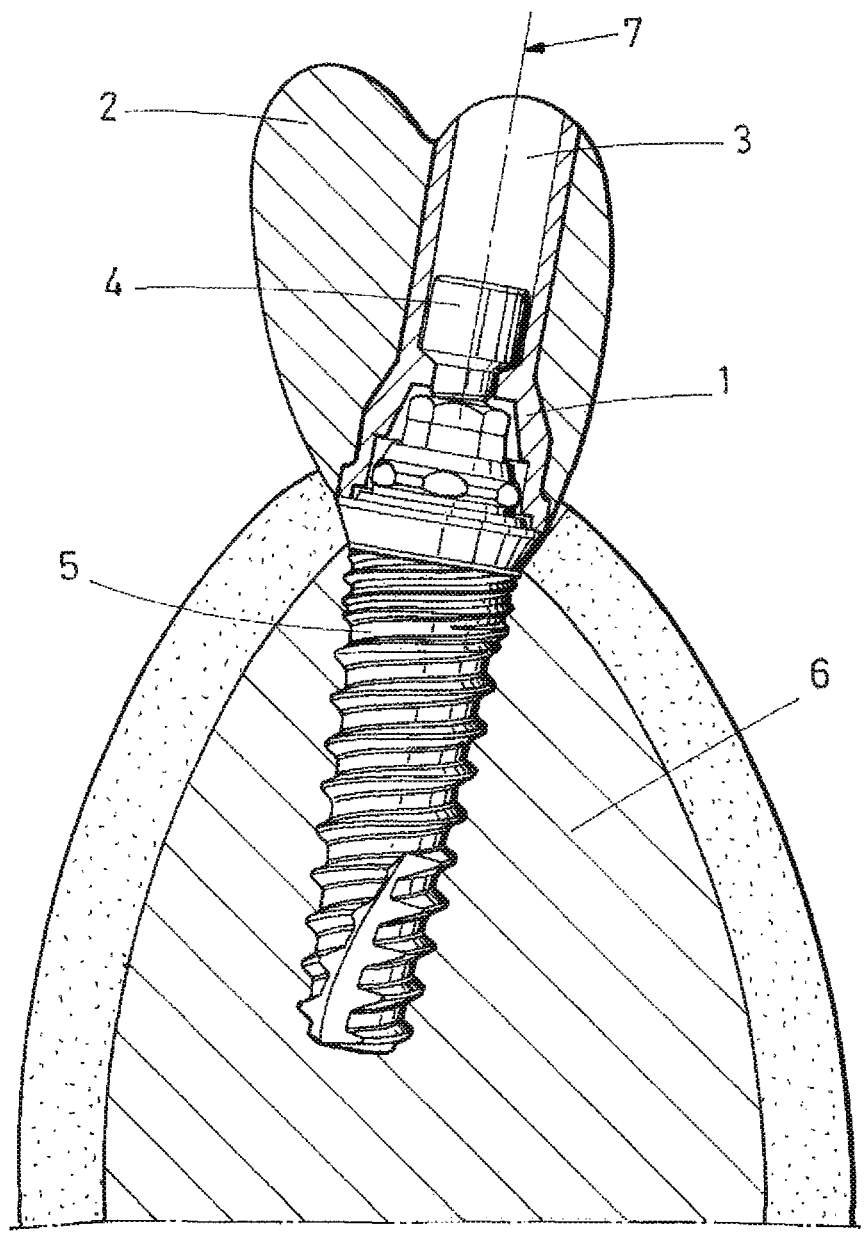
FIG. 3.2

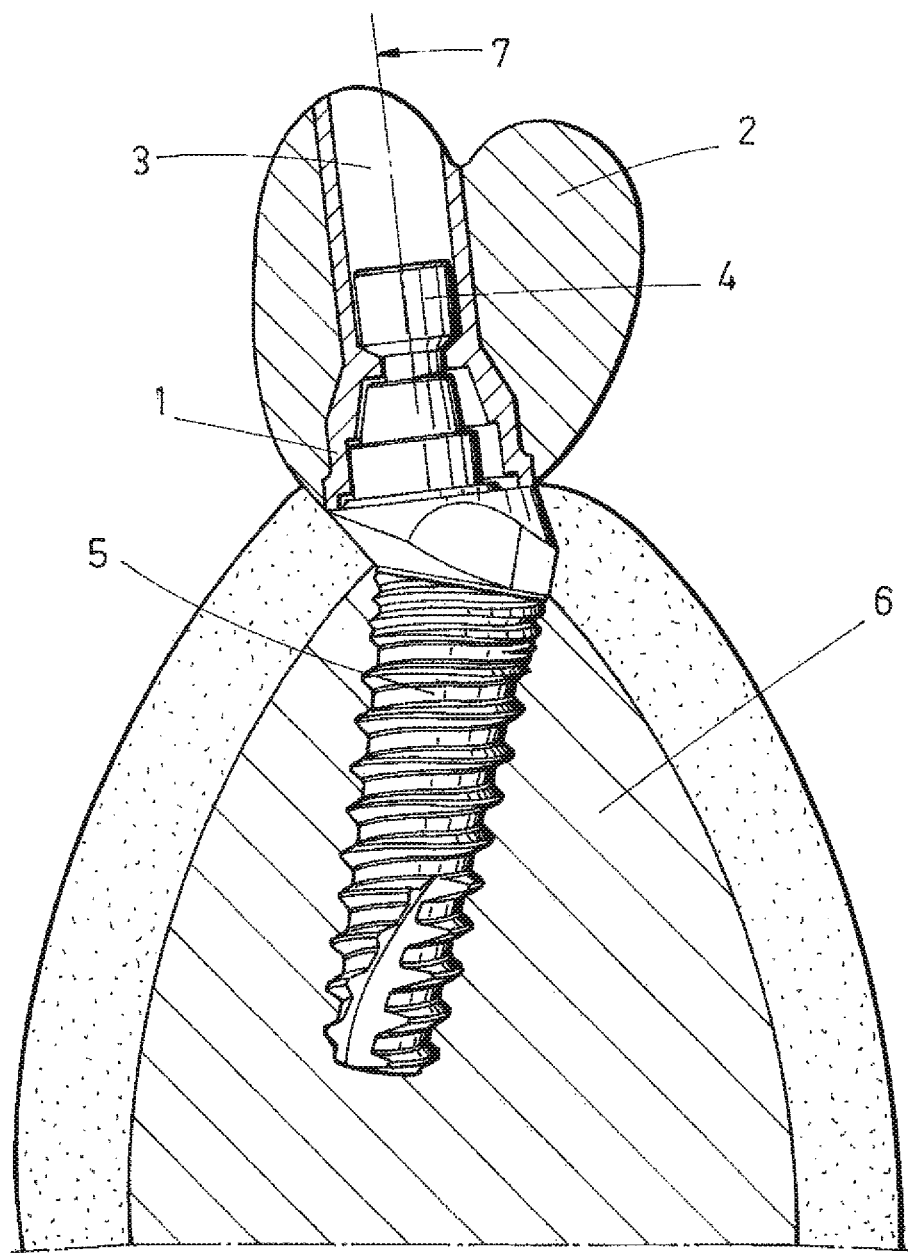
FIG. 3.3

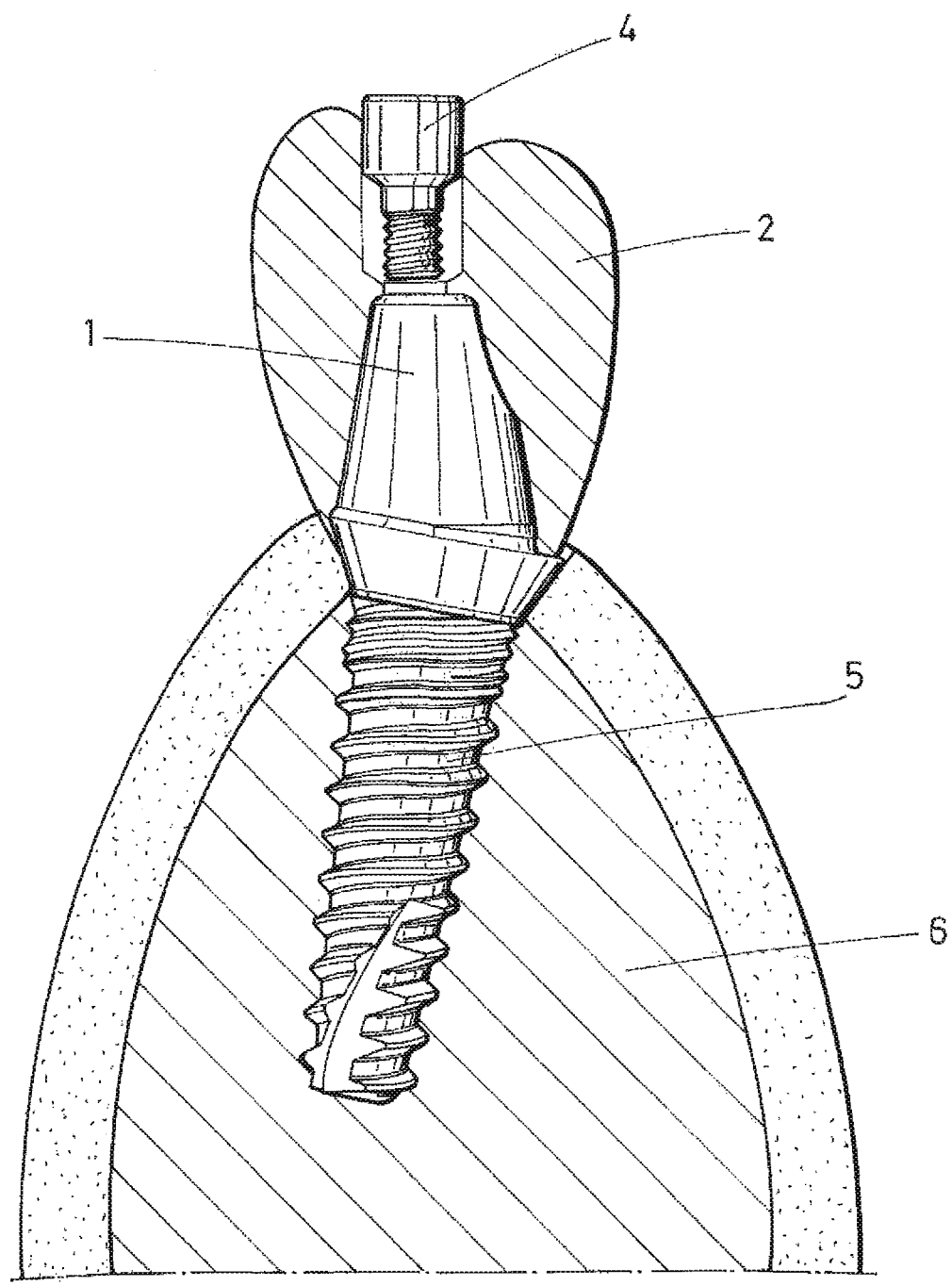
FIG. 3.4

DENTAL POST FOR SUPPORTING DENTAL PROSTHESES AND METHOD FOR THE PRODUCTION THEREOF

OBJECT OF THE INVENTION

The object of the present invention are customizable prosthetic abutments or dental posts intended for supporting dental prostheses.

More specifically, the posts of the invention are of the type which support the fixing of a prosthesis by means of a screw attachment, said attachment being located at the optimal site for each case, both from the mechanical viewpoint and from the aesthetic viewpoint.

BACKGROUND OF THE INVENTION

Implantology techniques currently allow replacing tooth roots by means of implants, to which the corresponding artificial dental pieces or prostheses are in turn coupled.

The implantation phases of said implants are generally summarized into an initial phase of implant insertion, followed by a subsequent immediate phase of osseointegration that involves a waiting time until the last phase of fixing the definitive prosthesis.

More specifically, the operations that are commonly carried out before the fixing of said definitive prosthesis are as follows:

1) stitching the soft tissue, keeping the implant covered for an osseointegration period and a later load implementation moment and subsequently opening the gum and placing the definitive prosthesis, or 2) not stitching the soft tissue, but rather leaving the implant exposed and in communication with the oral environment by means of:
   2a) a healing abutment fixed on the implant, performing stitching around same and applying functional load at the moment established in the planning of the case; or
   2b) placing a provisional prosthesis which is as similar as possible to the definitive prosthesis on the implant, which will allow early implementation with or without functional load but achieving an immediate aesthetic function.

That being said, both the provisional prosthesis which allows early implementation of the implant and the definitive prosthesis need to be attached or fixed on the post, or more accurately, on the post-implant assembly through the post. The techniques available today allow making said attachment:

by means of an attachment cement that gives rise to cement-retained prostheses; or in the form of a screw attachment by means of a retaining screw going through the prosthesis to the post, that gives rise to screw-retained prostheses in which standard prefabricated titanium posts are normally used.

Choosing one type of attachment or another will depend on a good number of factors. Screw-retained prostheses generally have the following advantages with respect to cement-retained prostheses:

1. Reversibility since there is the possibility of removing the screw and taking out the prosthesis, providing the possibility of cleaning the area and checking that there is no infection or any type of alteration whatsoever, being able to clinically act on the tissues around the post and implant.

2. Precision in the connection of the prosthesis to the post-implant and fixing on the post, a better control of the forces that are generated and transmitted to the implant-post-prosthesis shaft being obtained.

3. It has no drawbacks that are inherent to cement-retained prostheses such as:
   3a.—an amount of cement used usually migrates to the biological space, being able to cause an infection;
   3b.—there is always an attachment interface between the prosthesis and the cement post-implant that gradually degrades over time, being able to cause in patients with specific gum phenotypes, a chronic inflammatory reaction that would lead to a re-absorption of this cement and to a lower prosthesis stability and the invasion and intracoronal accumulation of possible bacteria in the attachment area which can lead to periodontal infections and subsequent implant loss.

Nevertheless, the use of the screw-retained prostheses also has a series of drawbacks such as:

1. The required level of fittings and tolerances both in design and in manufacture is very high, so methods, techniques and processes that are more complicated than in the case of cement-retained prostheses must be used; and 2. The aesthetic drawback, particularly in those cases in which the implant is in an inclined position in the bone with its axial axis towards the aesthetic front or side areas of the prosthesis, through which the retaining screw would pass, the hole for the entry of the screw remaining visible. In these cases, it is therefore necessary to carry out complementary techniques to cover or conceal this hole with the drawbacks in terms of materials and aesthetic termination.

This concern with respect to dental aesthetics in dentistry today has acquired a significant importance as patients become increasingly demanding of same, which involves a new challenge for health professional. For this reason, despite the fact that using screw-retained prostheses have the aforementioned advantages over cement-retained prostheses, many professionals chose to dispense with said screw-retained prostheses due to the need for using complementary techniques to close the hole for the passage of the screw to the post, choosing to use cement-retained prostheses instead.

On the other hand, an additional essential fact further regarded by the health professional when considering the post to be used is the fact that said post needs to be inclined or angled due to the relative and absolute position that must be taken up by the prosthesis in the patient's mouth for replacing the original dental piece and performing the same function.

As seen in FIGS. 1 and 2, these posts (1) can be both straight and angled, respectively, having the following characteristics in each case:

In the case of straight posts (1), such as that shown in FIG. 1, the axial axis (7) of said post (1) and that of the implant (5) both coincide with the outlet of the hole (3) for the entry of the retaining screw (4) for retaining the prosthesis (2) on the occlusal surfaces (top surfaces matching the antagonist tooth) in posterior teeth and inner buccal surfaces in anterior teeth.

In the case of angled posts (1), their axial axis (7), which now does not coincide with the axial axis of the implant (5), and the outlet of the hole (3) for the entry of the retaining screw (4) for retaining the prosthesis (2) coincide with the aesthetic side surfaces in posterior teeth and aesthetic front buccal surfaces in anterior teeth.

Typically, the elements involved in such attachments as can be seen in FIGS. 1 and 2 consist essentially of a post (1) supporting the prosthesis (2), which is screwed and retained on the implant (5) inserted in the bone (6) of the patient by means of a threaded element (9), wherein said post (1) has a threaded upper hole (8) for housing the retaining screw (4) with which the prosthesis (2) is retained on the post (1), the prosthesis (2) in turn having a through hole (3) for introducing the retaining screw (4) to the post (1) and wherein the axial axis of said through hole (3) coincides with that of the upper hole (8) of the post (1), as well as with the axial axis (7) of the post (1) itself when it is a straight post such as that shown in FIG. 1.

As mentioned above and as can be seen in FIG. 2, in the case of angled posts (1), the axial axis (7) thereof does not coincide with the axial axis of the implant (5), the threaded element (9) for attaching the post (1) to the implant (5) and the retaining screw (4) for attaching the post (1) to the prosthesis (2) therefore also having different axes of insertion with respect to one another.

As can also be inferred from the preceding FIGS. 1 and 2, the screw retention system involves a dual use of a retaining screw according to the parts to be attached, said attachment being:

a) the attachment of the prosthesis (2) to the post (1), in which case the use of a straight post or an angled post will be chosen taking into account the position of the implant (5) in the bone (6) and the direction of entry of the retaining screw (4) for retaining the prosthesis (2) on the post (1), which will be that of the axial axis (7) of the post (1).

b) the attachment of the post (1) to the implant (5), wherein the retention between them is always on the axial axis of the implant (5), both in the case of straight and angled post.

Although surgical techniques in implant insertion and positioning have currently improved significantly, there being previously adjusted guided surgical systems for positioning the implant in the bone, the final position of the implant will always depend on the remaining bone structure and therefore on the options of insertion, from a position axial to the masticatory load (the most favorable) of the dental group antagonist to the placed implant to inclined positions of the implant, usually ranging from 0° to 30°, 30° being the most unfavorable.

It is inferred from the foregoing that there will be a large number of positions and that it will therefore be impossible to have so many angled posts manufactured in a standard manner as to solve all the drawbacks that they have in implant rehabilitations by means of the corresponding prosthesis thereof.

The fact that there are, on one hand, different implant configurations (in their connection design) which will demarcate the final vertical position thereof in the bone, and on the other hand, various post configurations, is furthermore added to this situation, the post-implant assembly furthermore depending on aspects such as the height of the remaining bone, the amount of the remaining soft tissue and the height between the area under treatment and the antagonist dental group that must be in masticatory occlusion. In other words, there are many possible configuration requirements.

For all these reasons, the difficulty existing today for solving the different situations that may arise with the standard implants and abutments available on the market is obvious, there being a number of said situations in which it is impossible to find a dynamic and resolute position which allows applying the functional load with more balanced force moments and in accordance with the area to be rehabilitated and a screw insertion aesthetics with less drawbacks.

An example of how it is impossible to solve some situations due to the standard elements found on the market can be seen in FIGS. 3.1, 3.2 and 3.3. Said figures show a case wherein an implant is shown inserted in the bone with an angle of 10° with respect to the more favorable axial axis.

However, since a post angled 10° which allows correcting the insertion thereof is not available, this would force the professional to choose among three options:

a) using a cement-retention solution as can be seen in FIG. 3.1;

b) using a straight post (1) for screw-retained prosthesis (2) with entry of the retaining screw (4) through the outer side cusp, as can be seen in FIG. 3.2; or c) using a standard post (1) angled 15° such as that of FIG. 3.3, which would force leaving the entry of the retaining screw (4) through the inner or lingual cusp of the anatomical surface of the prosthesis (2).

Therefore, cases b) and c) show how the entry of the retaining screw (4) for retaining the prosthesis (2), in this case the crown of a molar tooth, is positioned on the cusp, when it should be in the area of the groove of the anatomical surface of the crown as indicated in FIG. 3.4.

This solution would therefore mean that in said cases b) and c), the prosthesis (2) must be reconstructed once the retaining screw (4) is placed, with the aesthetic drawbacks indicated above, to which the fact that the attachment between same would produce an unstable interface due to the use of different materials in the implant and reconstruction, must be added.

Furthermore, this position is neither ideal from the mechanical nor functional viewpoint since the cusps of molar teeth laterally withstand the shearing forces from chewing food causing the post to suffer more as it is has a non-ideal angle, and the risk of breakage is increased.

Therefore, given those biomechanical and aesthetic drawbacks, when facing such situations it is common to resort to cement-retention solutions such as that shown in said FIG. 3.1, situations which are very regular situations since the standard solutions are rarely the best option both from the aesthetic viewpoint and from the viewpoint of mechanical response that they must provide.

DESCRIPTION OF THE INVENTION

The dental post for supporting dental prostheses of the present invention solves the problems indicated above, allowing resorting to screw-retained prostheses in those dental implantology cases in which there are no standard solutions, wherein said post has the best fittings possible between all its parts, such that the end product benefits from all the advantages described above of such screw-retained fittings.

Specifically, the use of the post of the invention prevents compromising the aesthetic of the patient and allows complying with the particular mechanical requirements of each case, being able to change the spatial position, metrics and depth of the thread, therefore being the best possible solution for all.

To that end, the dental post of the present invention is characterized by comprising at least one upper hole into which a retaining screw is screwed for fixing the prosthesis on the post such that said upper hole can be located at any point of the surface of the post once said post has been customized in terms of the shape thereof and type of retention to the prosthesis depending on the mechanical and aesthetic needs of the type of rehabilitation suitable for each particular case.

The problems arising in those occasions in which, due to the position of the implant, the entry for the retaining screw for retaining the prosthesis on the post would be located in a visible site and therefore not aesthetically desirable, are thus solved, while at the same time allowing the positioning of the attachment between both elements, i.e., the post and prosthesis, in the optimal site from the mechanical performance viewpoint, thus complying with the ideal mechanical, functional and aesthetic requirements for each particular case.

Part of the invention also relate to a method for the manufacture of the dental post described above, which comprises the following steps:

the health professional taking an impression of the patient's mouth taking into account the particularities of each case, designing the post with the data of the patient obtained in the preceding step, customizing the shape thereof and type of retention to the prosthesis depending on the mechanical and aesthetic needs of the patient and calculating the ideal position of the upper hole by means of simulating the masticatory loads and the aesthetic requirements of the patient, transferring the file with the information obtained from the preceding step of designing to the step of planning for the manufacture of the post; and manufacturing the post itself using any of the known techniques for obtaining the best possible fitting between all the elements.

DESCRIPTION OF THE DRAWINGS

To complement the description that is being made and for the purpose of aiding to better understand the features of the invention according to a practical preferred embodiment thereof, a set of drawings is attached as an integral part of said description in which the following has been depicted with an illustrative and non-limiting character:

FIG. 3.1 shows a schematic front elevational view of an example of a cement-retained prosthesis.

FIG. 3.2 shows a schematic front elevational view of an example of a screw-retained prosthesis where the implant inserted in the bone has an angle of 10° and where the post is a straight post.

FIG. 3.3 shows a schematic front elevational view of an example of a screw-retained prosthesis where the implant inserted in the bone has an angle of 10° and where the post is an angled post.

FIG. 3.4 shows a schematic front elevational view of which would be the optimal position of a screw-retained prosthesis such as those of FIGS. 3.2 and 3.3.

Finally.

PREFERRED EMBODIMENT OF THE INVENTION

Figure 1:
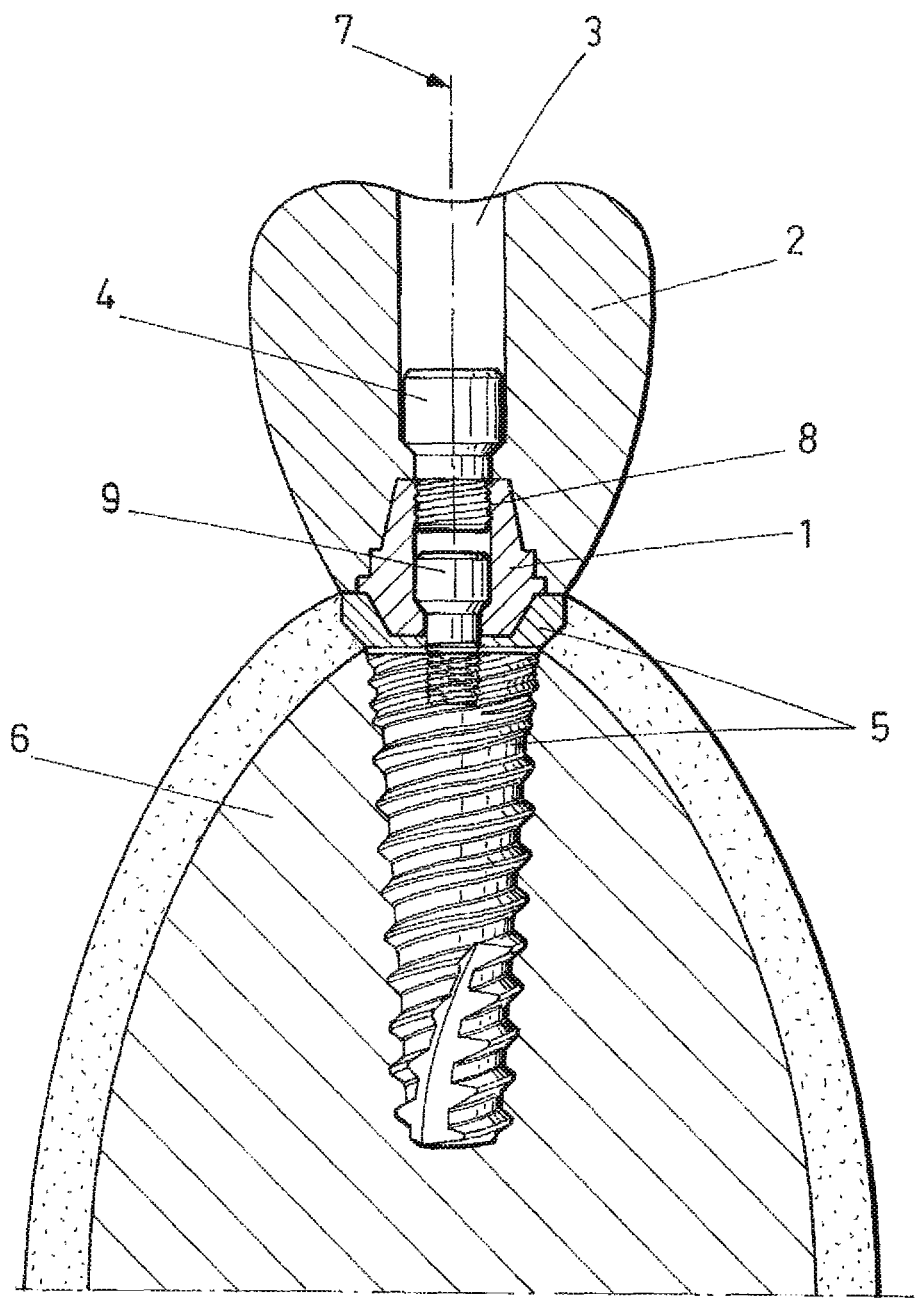
FIG. 1 shows a schematic front elevational view of a screw-retained prosthesis where the post is a straight post.
Figure 2:
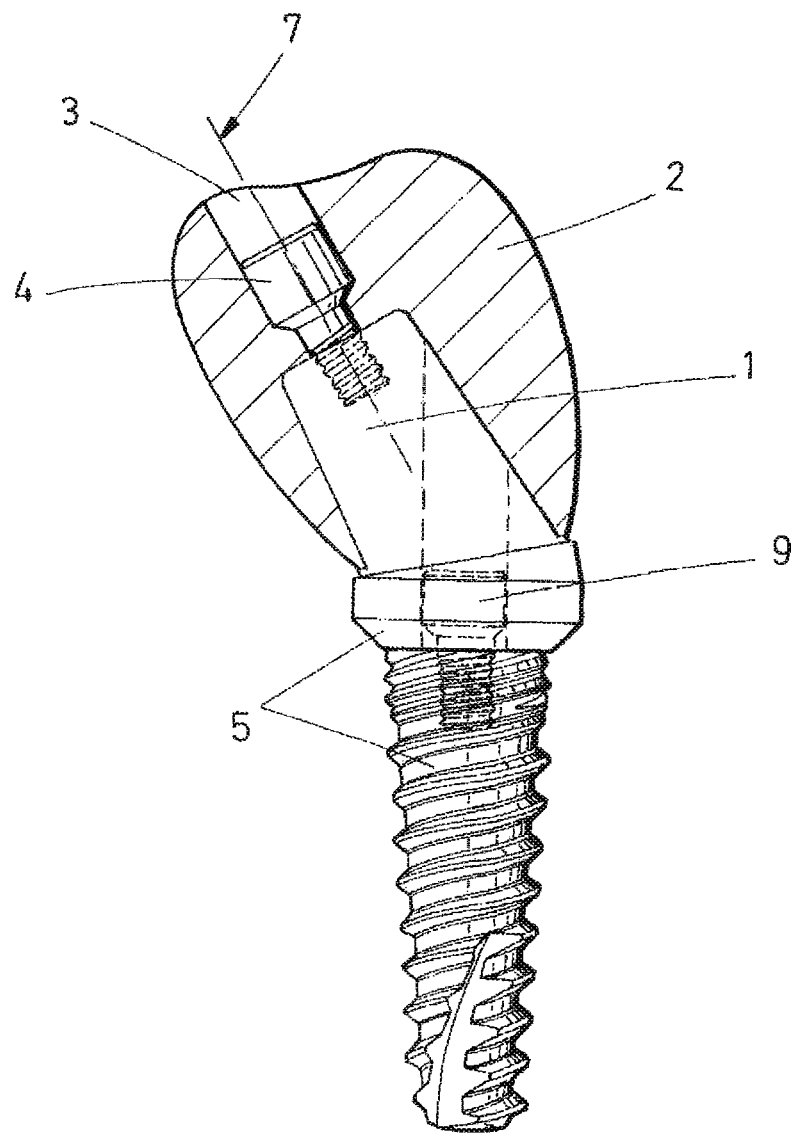
FIG. 2 shows a schematic front elevational view of a screw-retained prosthesis where the post is an angled post.
Figure 4:
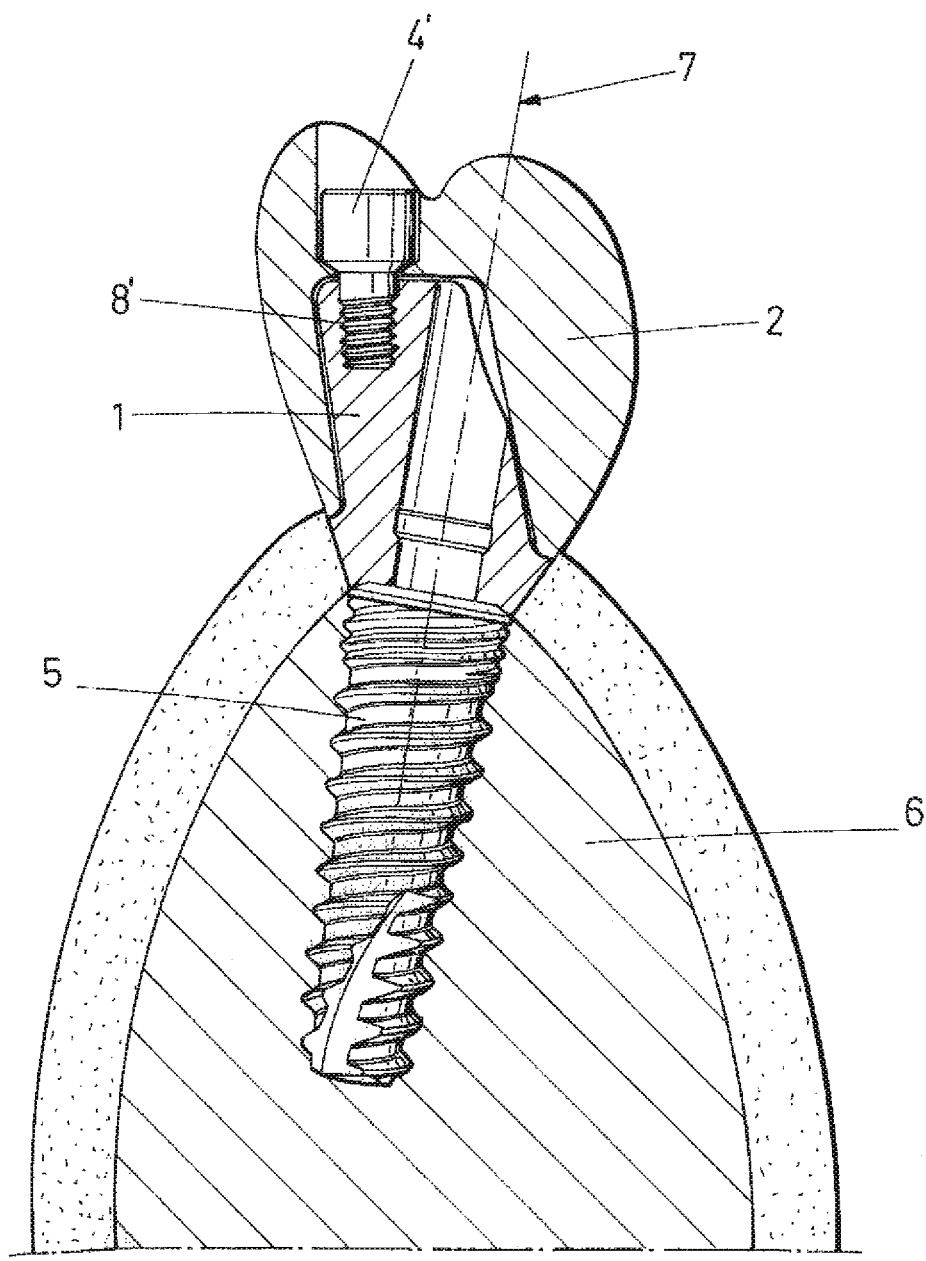
FIGS. 4 and 5 shows partial schematic elevational sections of respective embodiments where the position of the upper hole for housing the retaining screw for retaining the prosthesis on the post can be seen.
Figure 5:
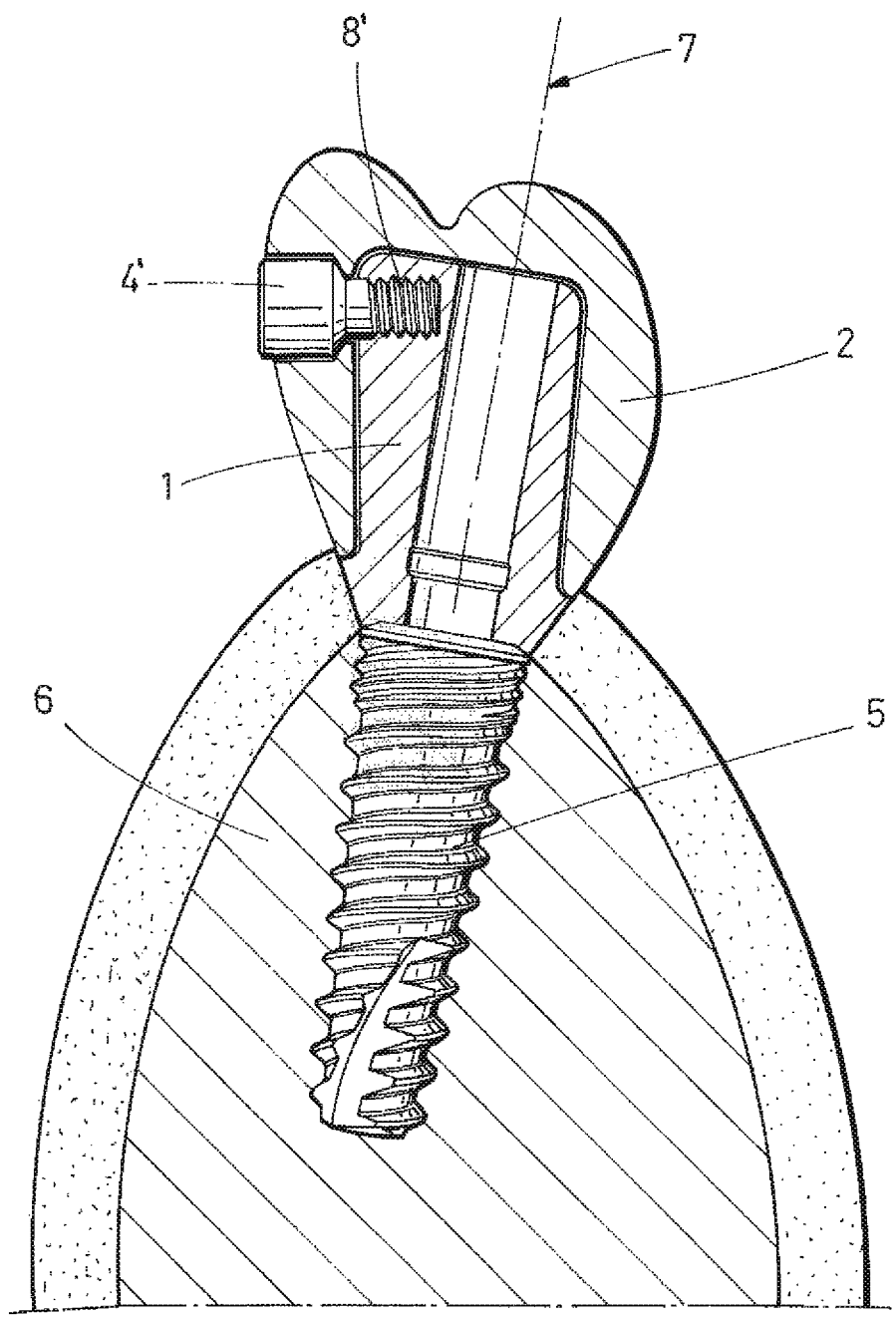
Figure 6:
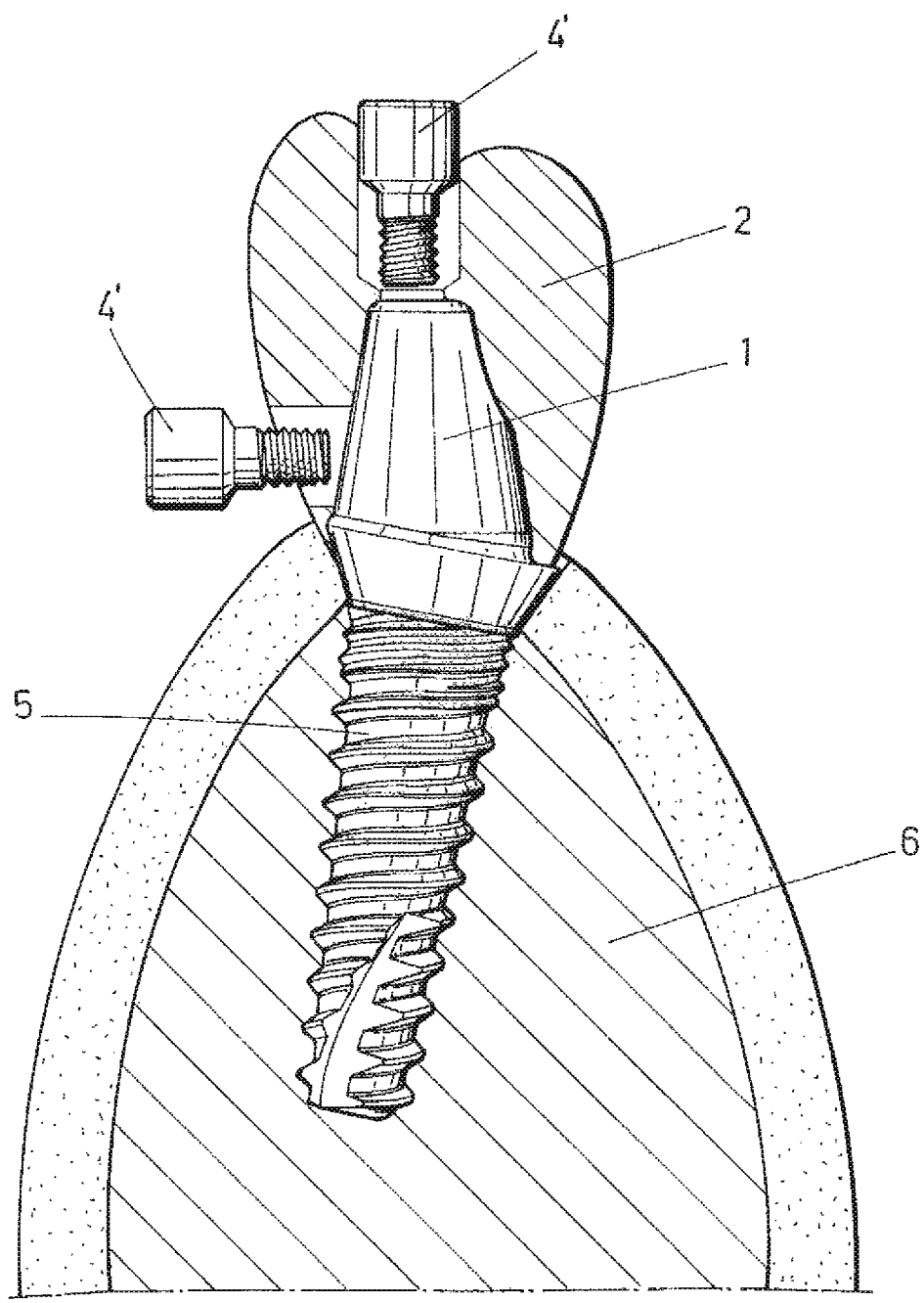
FIG. 6 shows a schematic elevational view of another possible embodiment of the invention with two possible options of positioning respective retaining screws for retaining the prosthesis on the post.

A preferred embodiment of the proposed invention is described in view of the drawings, particularly FIGS. 4, 5 and 6, wherein the post (1) comprises at least one upper hole (8') into which a retaining screw (4') is screwed for fixing the prosthesis (2) on the post (1) such that said upper hole (8') can be located at any point of the surface of the post once said post (1) has been customized in terms of the shape thereof and type of retention to the prosthesis (2) depending on the mechanical and aesthetic needs of the type of rehabilitation suitable for each particular case.

In terms of the method for the manufacture of the post (1) of the invention, said method comprises the following steps:

the health professional taking a manual or digital impression of the patient's mouth taking into account the particularities of each case.

designing the post (1) with the data previously obtained, customizing the shape thereof and type of retention to the prosthesis (2) depending on the mechanical and aesthetic needs of the patient and calculating the ideal position of the upper hole (8') by means of simulating the masticatory loads and the aesthetic requirements of the patient by means of a computer-aided design or CAD software, for example, subsequently transferring, through a suitable software such as a computer-aided manufacturing or CAM software, for example, the information from the step of designing to the step of planning for the manufacture of the end post (1) product, and wherein the database which is developed during CAD is processed by CAM for obtaining the data and instructions necessary for operating and controlling the manufacturing machinery, the material handling equipment and the automated tests and inspections for establishing product quality, thus obtaining a very high level of precision and reliability.

Once the file is obtained and prepared, it is subjected to the manufacturing process using any of the known techniques, such as for example the so-called rapid prototyping or laser sintering, such as for example 2, 3, 4 or 5 grade laser machines, jack, $CO_2$, or thermal laser machines, etc. or combinations thereof, by high precision machining, by sintering in furnace or electric discharge machining or any combination of these techniques such that the best possible fittings between all the elements are obtained. These posts (1) can be manufactured from a wide variety of metal materials, ceramic materials, plastic materials or combination thereof.

The invention claimed is:

1. Method for the manufacture of a post for supporting dental prostheses comprising at least one upper hole into which a retaining screw is screwed for fixing a prosthesis on the post, comprising:

taking an impression of a patient's mouth, simulating masticatory loads and aesthetic requirements of the patient, calculating an ideal position of the upper hole, designing the post with data of the patient obtained in the preceding steps, customizing the shape of the post and type of retention to the prosthesis, transferring a file with the design of the post obtained according to the preceding step of this method to a step of planning for the manufacture of the post; and manufacturing the post itself.

2. Method for the manufacture of a post for supporting dental prostheses according to claim 1, wherein a computer-aided design or CAD software is used in the step of designing the post.

3. Method for the manufacture of a post for supporting dental prostheses according to claim 1, wherein the step of transferring the information obtained in the step of designing the post is performed by a computer-aided manufacturing or CAM software and in that a database which is developed during CAD is processed by CAM to obtain a file with the data and the instructions necessary for operating and controlling manufacturing machinery, material handling equipment and automated tests and inspections for establishing product quality.

4. Method for the manufacture of a post for supporting dental prostheses according to claim 3, wherein for the manufacture of the post a rapid prototyping method, high precision machining, sintering in furnace or electric discharge machining or combinations thereof is used such that they allow a maximum level of fitting between elements of the dental prosthesis.

5. Method for the manufacture of a post for supporting dental prostheses according to claim 1, wherein for the manufacture of the post a rapid prototyping method, high precision machining, sintering in furnace or electric discharge machining or combinations thereof is used such that they allow a maximum level of fitting between elements of the dental prosthesis.

* * * * *